(12) United States Patent
Bernstein et al.

(10) Patent No.: US 6,222,190 B1
(45) Date of Patent: Apr. 24, 2001

(54) PHOTO ACOUSTIC INFRARED (IR) DETECTOR

(75) Inventors: Ralph Bernstein, Bekkestua; Alain Ferber, Haslum, both of (NO)

(73) Assignee: Leiv Eiriksson Nyfotek AS, Trondheim (NO)

( * ) Notice: Subject to any disclaimer, the term of this patent is extended or adjusted under 35 U.S.C. 154(b) by 0 days.

(21) Appl. No.: 09/254,987

(22) PCT Filed: Sep. 3, 1997

(86) PCT No.: PCT/NO97/00230

§ 371 Date: Mar. 17, 1999

§ 102(e) Date: Mar. 17, 1999

(87) PCT Pub. No.: WO98/12522

PCT Pub. Date: Mar. 26, 1998

(30) Foreign Application Priority Data

Sep. 19, 1996 (NO) .................................................... 963924

(51) Int. Cl.⁷ ........................ G01N 21/01; G01N 21/17
(52) U.S. Cl. ........................ 250/343; 250/344; 250/351
(58) Field of Search .................... 250/343, 344, 250/351

(56) References Cited

U.S. PATENT DOCUMENTS

| | | | |
|---|---|---|---|
| 4,740,086 | * 4/1988 | Oehler et al. | 250/343 |
| 4,866,681 | 9/1989 | Fertig | 367/140 |
| 4,903,248 | 2/1990 | Fertig | 367/140 |
| 5,616,826 | * 4/1997 | Pellaux et al. | 250/343 |
| 6,006,585 | * 12/1999 | Forster | 250/343 |

FOREIGN PATENT DOCUMENTS

| | | | |
|---|---|---|---|
| 41 16 280 A1 | 12/1991 | (DE) | G01F/1/56 |
| 2 218 198A | 8/1989 | (GB) | G01B/11/00 |
| WO 96/24831 | 8/1996 | (WO) | G01N/21/17 |

OTHER PUBLICATIONS

Patent Abstracts of Japan, vol. 10, No. 19–P–42, Abstract of JP 60–173443A (Jun. 09, 1985).

* cited by examiner

*Primary Examiner*—Constantine Hannaher
*Assistant Examiner*—Otilia Gabor
(74) *Attorney, Agent, or Firm*—Duane, Morris & Heckscher LLP

(57) ABSTRACT

Photo acoustic infrared (IR) detector including a chamber for receiving a gas or gas mixture, a window for allowing pulsed or modulated IR radiation into the chamber, and a pressure sensor adapted to measure pressure changes in the chamber as a consequence of absorbed IR radiation. A generally plate-shaped main part has a recess or bore for substantially forming the chamber whereby the window closes the chamber at one side of the main part and whereby the pressure sensor is of the miniature type and is located at the opposite side of the main part in relation to said one side so that the pressure sensor communicates with and closes the chamber at the opposite side, except for a venting channel for the chamber. A cap is provided at said opposite side of the main part so that it encloses the pressure sensor and forms a gas space communicating with the chamber through the venting channel and being substantially larger than the gas volume in the chamber.

16 Claims, 2 Drawing Sheets

PHOTO ACOUSTIC INFRARED (IR) DETECTOR

Figure 1:
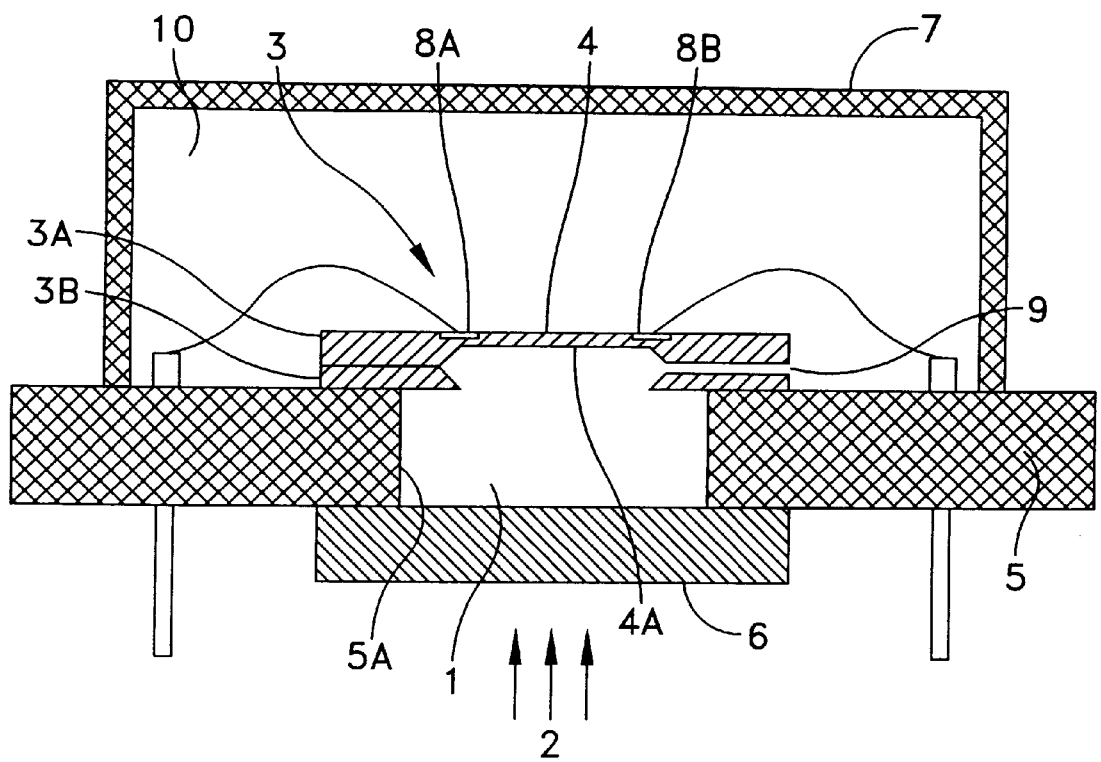

Photo acoustic techniques are based on the heat effect being known as the photo-thermal effect. These techniques take advantages of the principle that absorbed radiation energy, in particular from infrared (IR) radiation results in pressure variations in a constant gas volume, whereby the pressure variations are proportional to the amount of energy absorbed. These pressure variations can then be detected by means of a sensitive pressure sensor.

This invention is directed to a photo acoustic infrared (IR) detector comprising a chamber for receiving a gas or gas mixture, a window for pulsed or modulated IR radiation into the chamber, and a pressure sensor adapted to detect or measure pressure changes in the chamber as a consequence of absorbed IR radiation. In the practical use of such a detector there can be the question of measuring or detecting infrared radiation in general, but a specific and important field of use relates to detection or measurements of gas or gas mixtures, e.g. with respect to air quality or air pollution.

Examples of known uses of such photo acoustic techniques are found, inter alia, in patent publication U.S.-H651 and in an article by C. F. Dewey Jr., R. D. Kamm and C. E. Hackett: Acoustic amplifier for detection of atmospheric pollutants, Appl. Phys. Lett., Vol. 23, No. 11, December 1973.

The present invention aims at substantial improvements in a photo acoustic detector as referred to above. An important object of the invention is to provide a detector design that can be manufactured in a simple and rational manner, among other things by employing standard components being in common use within the semiconductor technology and within electronics in general. It is possible to make photo acoustic detectors based on the invention, in miniature designs, being based upon the construction of the actual pressure sensor element by means of silicium i.e. silicon or similar materials, which e.g. are employed within the semiconductor technology.

On the above background the photo acoustic infrared detector according to the invention comprises novel and specific features in the form of a generally plate-shaped main part having a recess or bore for substantially forming the chamber, whereby the window closes the chamber at one side of the main part and whereby the pressure sensor is of the miniature type and is located at the opposite side of the main part in relation to said one side, so that the pressure sensor communicates with and closes the chamber at the opposite side, except for a venting channel for the chamber, and a cap being provided at said opposite side of the main part so that it encloses the pressure sensor and forms a gas space communicating with the chamber through the venting channel and being substantially larger than the gas volume in the chamber.

In a preferred embodiment of the detector according to the invention, the pressure sensor is manufactured of silicium in planar technology, i.e. a technology being well known and well developed within the semiconductor field.

In a further particularly preferred embodiment of the invention, the main part and the cap are in the form of components known per se for a standard encapsulation, whereby the main part is formed by the bottom of the standard capsule. In such a bottom the chamber can be formed in various ways, inter alia as an opening bored through the bottom.

Normally the pressure sensor will comprise a membrane structure with sensor elements incorporated therein or applied thereto. In order to generate a measuring signal corresponding to the membrane oscillations resulting from pressure changes in the chamber, various sensor principles can be contemplated, e.g. a piezo-resistive or capacitive measurement principle. In the exemplary embodiment to be described more closely below, piezo-resistive sensor elements are provided. Such principles and techniques are well known in connection with silicium pressure sensors and microphones or the like, and will not be discussed more closely here.

The design and manufacture of photo acoustic infrared and gas sensors based on silicium micromechanics involve several substantial advantages. These gas sensors are cheap in production and can be utilized advantageously for providing highly miniaturized photo acoustic detectors.

Figure 2:
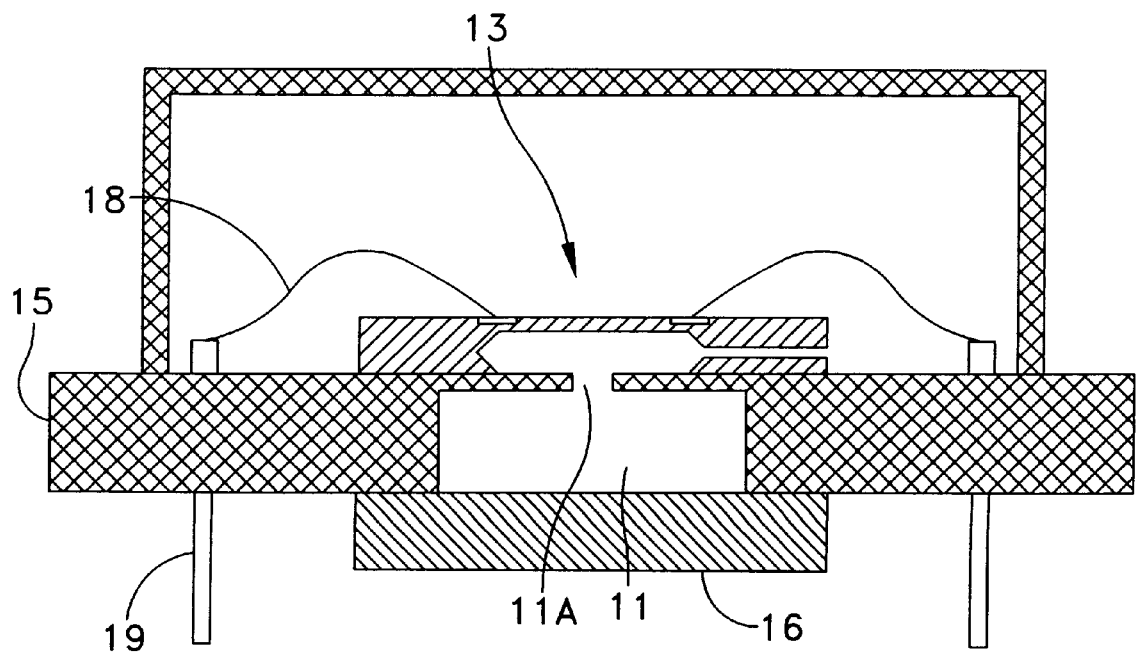
Figure 3:
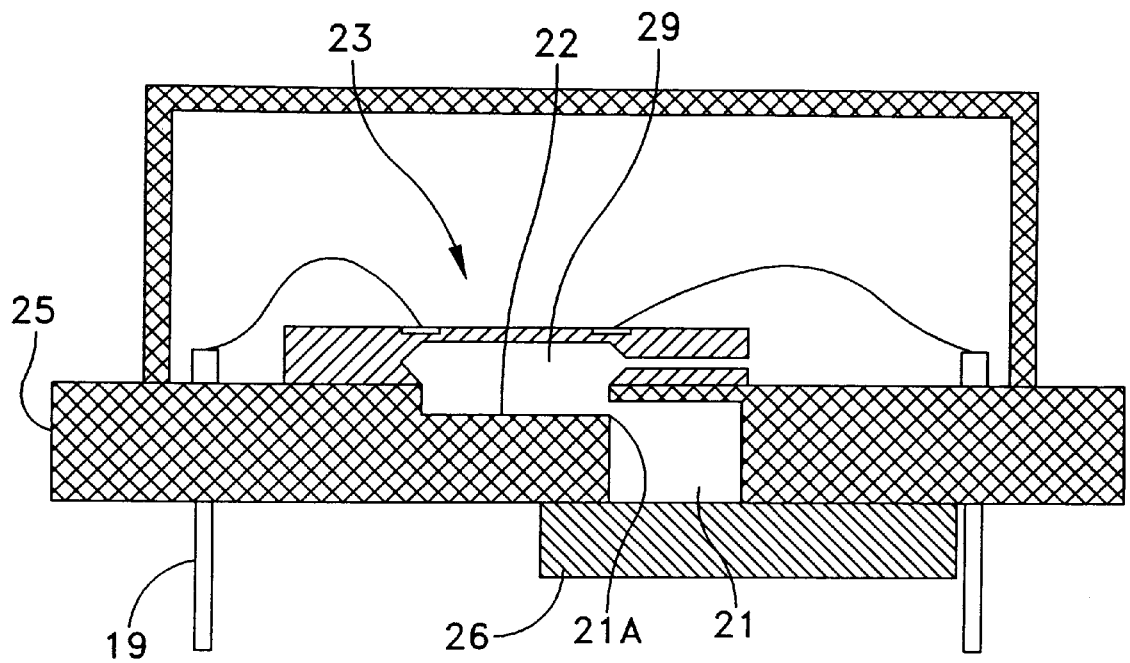
Figure 4:
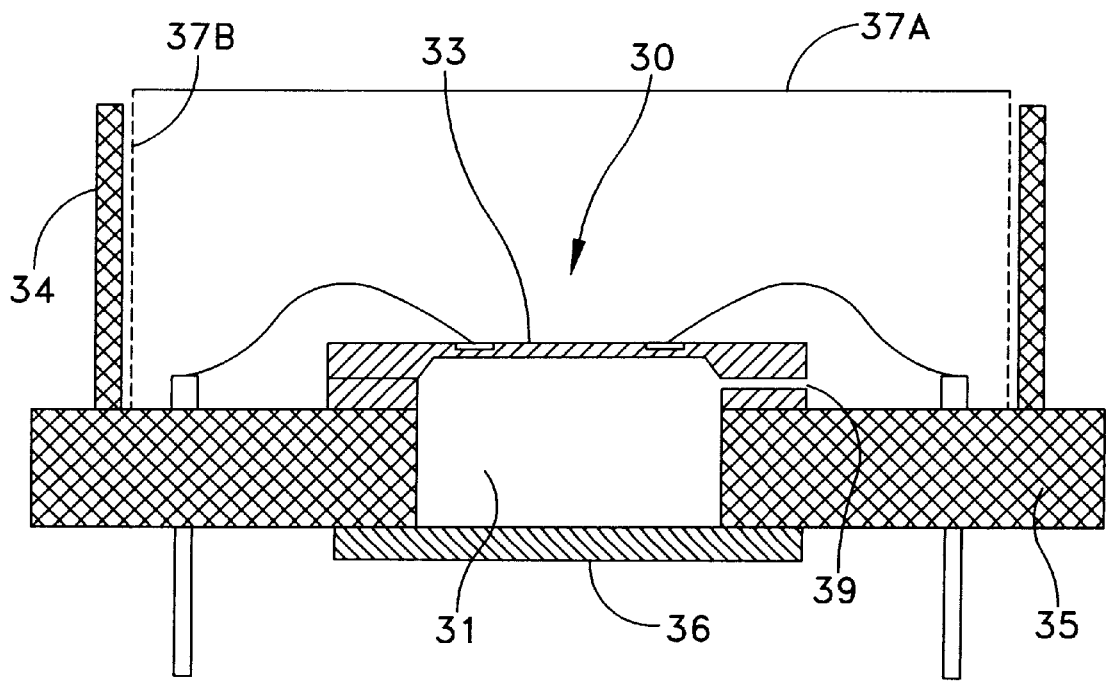

In the following description the invention will be explained more closely with reference to the drawing, which much simplified and schematically, but at a substantially enlarged scale, shows a cross section through a detector structure based on the invention, in three different embodiments:

FIG. 1 shows a first and usually preferred embodiment according to the invention, FIG. 2 shows a second embodiment of the detector according to the invention, FIG. 3 in a corresponding way shows a third embodiment, and FIG. 4 shows a fourth embodiment of the detector according to the invention.

The detector design in FIG. 1 can e.g. be based on a standard encapsulation of the type TO-8, whereby the numeral 8 in this type designation indicates the diameter of the actual cap or capsule in mm. The invention will also be able to employ smaller cap diameters, such as 6 mm or even 4 mm, which according to present technology is to be regarded as a minimum for the infrared detectors being of interest here.

The figure of drawings shows an absorption chamber 1 formed in a main part 5 which is the bottom plate in the standard capsule component. In the main part or bottom 5 there is thus bored a through hole 5A, which can have a diameter of e.g. 3.4 mm at a bottom plate tickness of e.g. 1.5 mm. At one side of the main part 5 the chamber 1 is confined and closed by a window 6 that is transparent to the IR radiation concerned, as illustrated with arrows 2 in the drawing. Window 6 can suitably be made of sapphire with a thickness of approximately 1 mm. It is an advantage to apply an anti-reflection coating on window 6.

At the other side of the main part 6, i.e. at the upper side according to the drawing, there is located a pressure sensore generally denoted 3, so that chamber 1 will be completely closed except for a venting channel 9 being provided in or in association with the pressure sensor 3.

Moreover at the upper side of main part 5 there is shown a cap 7 which corresponding to the main part or bottom plate 5 preferably is in the form of a standard component as explained above. In a common or standarized manner cap 7 can be tightly attached to the upper side of main part 5. Accordingly pressure sensor 3 will be completely enclosed by cap 7, with a relatively large gas space 10 surrounded by cap 7 around pressure sensor 3. Thus chamber 1 communicates with gas space 10 through the venting channel 9.

For the purpose for example, of measuring high consentrations of $CO_2$ in buildings, i.e. for well-being or comfort reasons, it is expedient in this particular example to fill gas space 10 with a gas mixture of 15% $CO_2$ in argon. During sealing of the cap 7 on main part 5, this gas mixture will leak from space 10 into absorption chamber 1 through venting channel 9, so that this desired gas mixture will also fill chamber 1.

In order that the detector structure described, with associated pressure sensor 3, shall have the intended function by absorbing pulsed or modulated infrared radiation 2 entering into chamber 1 through window 6, gas space 10 must not have influence on the dynamic changes in the gas volume in chamber 1 as a result of the incident pulsating radiation. Accordingly venting channel 9 is dimensioned and arranged so as to have a time constant with respect to pressure variations, being several times longer than the modulation period of the IR radiation. Preferably the time constant of the venting channel is at least ten times larger than the radiation period.

In this case pressure sensor 3 is built up of silicium and is based on piezo-resistive detector elements. Sensor 3 consists of two silicium members 3A and 3B being essentially plate-shaped. Member 3B is a support member being attached to the upper side of main part 5, e.g. by gluing, welding, brazing or bonding. Similar techniques can also be employed for attaching window 6 to the underside of main part 5. The upper silicium member 3A is joined in a similar manner to member 3B and comprises the more functional aspects of pressure sensor 3. Thus in member 3A there is provided a membrane 4 with piezo-resistive elements 8A and 8B. It is obvious that although only two such elements are shown in the drawing, there will usually in practice be included several resistive elements, e.g. four such elements in a bridge coupling or the like. When manufacturing silicium members 3A and 3B in the shapes shown, anisotropic etching can be employed, as known from semiconductor technology. This in particular applies to membrane 4 and venting channel 9. In this connection it is clear that the relative dimensions in actual practice can deviate significantly from what is schematically known as an example in the drawing, whereby e.g. membrane 4 will be very thin in many practical designs.

Except for the inside of window 6, it appears from the drawing that internally chamber 1 is coated with a reflecting aluminum coating 4A, whereby such a reflecting layer covers at least the internal surface portion of sensor 3 which is constituted by membrane 4. Coating 4A serves to reflect incident IR radiation 2 back and out through window 6.

As an alternative to this return reflection of IR radiation, both pressure sensor 3 and cap 7 can be manufactured at least in part of a material being transparent to IR radiation, so that this will be able to penetrate directly through the detector from the underside and out at the upper side (not illustrated in the drawing), for the intended absorption in chamber 1. The opposite radiation direction normally will not be practical because of the absorption being so to speak useless, that will take place in gas space 10. As regards the pressure sensor 3, it will be in particular membrane 4 which is of interest for this through-going radiation, when a transparent material in sensor 3 is used.

In the modified embodiment of FIG. 2 there are also in principle the main features of the design as shown in FIG. 1, among other things by showing an enclosed gas space around the actual pressure sensor 13. This is located on the upper side of a main part 15, being at its underside provided with a window 16 as in the embodiment of FIG. 1. However, chamber 11 in FIG. 2 is not as chamber 1 in FIG. 1, obtained by a full through opening or bore in main part 15, but in the form of a recess communicating through a smaller hole 11A with a smaller space in front of the membrane in sensor 13. Otherwise FIG. 2 shows an electric lead 18 and an associated contact pin 19 for one of the piezo-resistive elements in sensor 13. Corresponding elements are also shown in FIGS. 1 and 3.

In the further embodiment or variant shown in FIG. 3, main part 25 has also a not through-going recess in order to form a chamber 21. At the underside this is closed with a window 26, and communicates upwards through a passage 21A with a space 29 in front of the membrane in pressure sensor 23. Space 29 is formed in part by a smaller recess 22 formed from the upper side of main part 25. In contrast to the preceding embodiments, where window and pressure sensor are located substantially right opposed to each other, FIG. 3 shows a mutually displaced relationship between window 26 and pressure sensor 23. Although this embodiment in several aspects will be somewhat more complicated than the two preceding embodiments, it can represent a design being feasible in actual practice.

The particular embodiment shown in FIG. 4 comprises main elements corresponding to the preceding embodiments, i.e. a main part 35, a window or filter 36, a pressure sensor 33, a chamber 31, a gas space 30 and a venting channel 39 allowing the gas space to communicate with the chamber. What is specific in the embodiment of FIG. 4, is that certain wall portions of the cap, as illustrated at 37B, are adapted to permit diffusion of gas between gas space 30 and the ambient atmosphere. The cap wall portion 37B, which can run cylindrically around the whole capsule, thus is shown with a perforation and on the outside of this wall portion there is applied a diffusion material 34 that serves to protect against penetration of dust and other particles into the space 30. This diffusion material 34 can be selected among available filter materials, e.g. such materials being employed in coal filters, or they can be based on felt. Coal filter materials can also have a favourable influence with respect to preventing moisture penetration. Felt on the other side is a suitable material when dry air or gas is concerned.

With the structure being illustrated as an example in FIG. 4, the gas to be subjected to measurement, will be able to enter from the ambient atmosphere by diffusion through the cap wall portions 37B with diffusion material 34, and then from gas space 30 through venting channel 39 into the actual detection or measurement chamber 31. In many cases such an embodiment can be more favourable than the embodiments described above, where the cap around the gas space is considered to close this in a sealing manner. This gas penetration can take place by "natural" passive venting or as a result of a forced, active gas flow. Moreover it is obvious that diffusion can take place in both directions through wall portions 37B.

In addition to the modifications mentioned above, it is clear that e.g. the filling of gas or gas mixture can vary significantly depending on which particular uses the detector is intended for. The actual pressure in gas space 10 (FIG. 1) and thereby the static pressure in absorption chamber 1, can also be adjusted as desired, inter alia by employing a pressure lower than the atmospheric pressure, e.g. ⅓ of the atmospheric pressure.

What is claimed is:

1. Photo acoustic (IR) detector comprising a chamber for receiving a gas or gas mixture, a window for allowing pulsed or modulated IR radiation into the chamber, and a pressure sensor adapted to detect or measure pressure changes in the chamber as a consequence of absorbed IR radiation, further comprising a generally plate-shaped main part having a recess or bore for substantially forming the chamber, whereby the window closes the chamber at one side of the main part, and whereby the pressure sensor is of the miniature type and is located at the opposite side of the main part in relation to said one side, so that the pressure sensor communicates with and closes the chamber at the opposite side, except for a venting channel for the chamber, and a cap provided at said opposite side of the main part so that it encloses the pressure sensor and forms a gas space communicating with the chamber through the venting channel and being substantially larger than the gas volume in the chamber.

2. Detector according to claim 1, wherein the miniaturized pressure sensor is manufactured of silicium in planar technology.

3. Detector according to claim 1, wherein the main part and the cap are in the form of components as known per se for a standard encapsulation, whereby the main part forms the bottom of the standard capsule.

4. Detector according to claim 1, wherein the cap closes the gas space in a sealing manner against the ambient atmosphere.

5. Detector according to claim 1, wherein the cap comprises wall portions making possible diffusion of gas, but not dust and other particles, between the gas space and the ambient atmosphere.

6. Detector according to claim 1, wherein the venting channel is dimensioned and arranged so as to have a time constant with respect to pressure variations, being several times longer than the modulation period of the IR radiation.

7. Detector according to claim 1, wherein a surface portion of the pressure sensor internally in the chamber, is provided with a reflecting coating so as to reflect incident IR radiation back out through the window.

8. Detector according to claim 1, wherein the pressure sensor and the cap consist at least partially of a material being transparent to IR radiation, so that IR radiation can pass out of the chamber through the transparent material.

9. Detector according to claim 1, wherein said recess or bore is in the form of a through opening in the main part.

10. Detector according to claim 1, wherein said recess or bore for the chamber is formed from said one side of the main part and communicates with the pressure sensor through a hole or a passage.

11. Detector according to claim 10, wherein the window and the pressure sensor are mutually displaced at either side of the main part.

12. Detector according to claim 10 wherein the window and the pressure sensor are mutually displaced at either side of the main part, and said passage is directed mainly laterally in the plane of the main part.

13. Detector according to claim 1, wherein the pressure sensor is composed of two mainly plate-shaped members of silicium.

14. Detector according to claim 13, wherein the venting channel is formed in the joining surface of one of the members.

15. Detector according to claim 1, wherein the venting channel is dimensioned and arranged so as to have a time constant, with respect to pressure variations, at least ten times larger than the modulation period of the IR radiation.

16. Detector according to claim 1, wherein said recess or bore is in the form of a through opening in the main part and includes the window and the pressure sensor located directly opposite one another.

* * * * *